US008889182B2

(12) United States Patent
Bresciani et al.

(10) Patent No.: US 8,889,182 B2
(45) Date of Patent: Nov. 18, 2014

(54) PROCESS OF THERMODYNAMICAL ACTIVATION OF WATER-INSOLUBLE DRUGS LOADED INTO CROSS-LINKED POLYMERS

(75) Inventors: Massimo Bresciani, Trieste (IT); Lorenzo Magarotto, Sistiana (IT); Luca Dobetti, Trieste (IT)

(73) Assignee: Aptalis Pharma Limited, Bray (IE)

( * ) Notice: Subject to any disclaimer, the term of this patent is extended or adjusted under 35 U.S.C. 154(b) by 1045 days.

(21) Appl. No.: 10/481,938

(22) PCT Filed: Jun. 3, 2002

(86) PCT No.: PCT/EP02/06052
§ 371 (c)(1),
(2), (4) Date: Dec. 24, 2003

(87) PCT Pub. No.: WO03/002097
PCT Pub. Date: Jan. 9, 2003

(65) Prior Publication Data
US 2004/0213840 A1    Oct. 28, 2004

(30) Foreign Application Priority Data

Jun. 29, 2001 (IE) .................................. 20010628

(51) Int. Cl.
*A61K 9/14*    (2006.01)
(52) U.S. Cl.
CPC ..................................... *A61K 9/146* (2013.01)
USPC ......................................... 424/464; 264/109
(58) Field of Classification Search
CPC ..................................................... A61K 9/146
USPC .......................................... 424/451, 464, 489
See application file for complete search history.

(56) References Cited

U.S. PATENT DOCUMENTS

| 4,639,370 | A | * | 1/1987 | Carli ........................... 514/772.5 |
| 5,225,192 | A | * | 7/1993 | Lovrecich ..................... 424/484 |
| 5,275,824 | A | * | 1/1994 | Carli et al. .................... 424/490 |
| 5,449,521 | A | * | 9/1995 | Lovrecich |
| 5,849,329 | A | * | 12/1998 | Conte et al. ................... 424/469 |
| 6,355,273 | B1 | * | 3/2002 | Carli et al. .................... 424/489 |

FOREIGN PATENT DOCUMENTS

| DE | 2634004 | 2/1978 |
| DE | 3320583 | 12/1984 |

OTHER PUBLICATIONS

Hancock, Journal of Pharmaceutical Sciences, 86, 1997.*
Nifedipine, Sigma, 1996.*
Colombo, I., "Differential Scanning Calorimetry of Drug Solid Dispersions in Crosslinked Polymers," 4th International Conference on Pharmaceutical Technology, Paris, France (Jun. 1986).
Blachere, J.R. et al., "The Freezing Point of Water in Porous Glass," *Journal of American Ceramic Society*, vol. 55, No. 6, pp. 306-308 (Jun. 1972).
Brun, M. et al., "No. 130—Changement D'Etat Liquide—Solide Dans Les Milieux Poreux. I. Étude expérimentale de la solidification de l'eau et du benzène," *Journal De Chimie Physique*, vol. 70, No. 6, pp. 973-978 (1973).
Brun, M. et al., "No. 131—Changement D'Etat Liquide—Solide Dans Les Milieux Poreux. II. Étude théorique de la solidification d'un condesat capillaire," *Journal De Chimie Physique*; vol. 70, No. 6, pp. 979-989 (1973).
Hsia, D.C. et al., "Determination of Energy Change Associated with Dissolution of a Solid," *Journal of Pharmaceutical Sciences*, vol. 66, No. 7, pp. 961-965 (Jul. 1977).
Carli, F. et al., "Physical state of drug loaded into silica gel carriers," *Acta Pharm. Jugosl.*, 38, pp. 361-371 (1988).
Brun, M. et al., "No. 130—Changement D'État Liquide—Solide Dans Les Milieux Poreux. I. Étude expérimentale de la solidification de l'eau et du benzène," *Journal De Chimie Physique*, vol. 70, No. 6, pp. 973-978 (1973).
Brun, M. et al., "No. 131—Changement D'État Liquide—Solide Dans Les Milieux Poreux. II. Étude théorique de la solidification d'un condesat capillaire," *Journal De Chimie Physique*, vol. 70, No. 6, pp. 979-989 (1973).

* cited by examiner

*Primary Examiner* — Robert A Wax
*Assistant Examiner* — William Craigo
(74) *Attorney, Agent, or Firm* — Christensen O'Connor Johnson Kindness PLLC

(57) ABSTRACT

The present invention refers to a process to prepare a highly activated composite of one or more water-insoluble drugs, said process comprising the steps of: (a) subjecting said water-insoluble drug and a cross-linked polymer to co-grinding; (b) exposing the ground product of step a. to contact with water or water vapors. The resulting composite contains large amounts of drug in the easily soluble amorphous form, reduced amounts of drug in the nanocrystalline form, and is substantially free from practically insoluble drug crystals.

10 Claims, No Drawings

PROCESS OF THERMODYNAMICAL ACTIVATION OF WATER-INSOLUBLE DRUGS LOADED INTO CROSS-LINKED POLYMERS

STATE OF THE ART

Oral delivery of poorly soluble drugs has become, in the last years, one of the most challenging problems for advanced pharmaceutical research. Usually, drugs with low water solubility show poor bioavailability and a high variability of plasma levels among subjects. This in turn leads to formulations with high drug content which often must be delivered repeatedly to obtain and maintain therapeutic plasma levels.

Several studies have been made with the purpose of improving the solubility of these drugs by physical means, without resorting e.g. to chemical derivatisation or the use of additional chemicals.

The unfavourable biopharmaceutical behaviour of poorly soluble drugs is strictly correlated with well defined physical-chemical characteristics. Drug uptake can occur in different ways but, for small synthetic molecules, absorption via a non-saturable passive process (diffusion through the GI barrier) plays a primary role. The ability of poorly water soluble drugs to be passively absorbed is strictly dependent on their physical properties, such as steric hindrance, crystal form, solubility, lipophily, wettability and surface area.

Due to their organised lattice-like structures, drug crystals require a large amount of energy to completely dissolve. The total energy required for dissolving a solid drug is the sum of many contributions, namely surface interaction (generation of a new solid-liquid interface), fusion (crystal lattice fracture), solvation of each single solute molecule and mass transfer or diffusion into the solvent (D. C. Hsia et al., *J. Pharm. Sci.* 66, 961, 1977).

The first two energy steps (surface interaction and fusion) necessary to reach the drug dissolution can be eliminated by forming an amorphous phase of the drug (state with an increased thermodynamic activation) or strongly reduced by the presence of drug nanocrystals (crystals having dimensions of nanometers). Amorphisation, and formation of nanocrystals at a less extent, results in drug solubilisation kinetic, having dissolution rate and supersaturation concentrations, that is much higher than that obtainable with the differently formulated drug in its crystalline state. This allows a strong increase of the drug effects "in vivo" by enhanced bioavailability, reduction of the onset of action ($t_{max}$) and decrease of the variability between subjects.

From these considerations, the following rank of solid state thermodynamic activation can be described: amorphous>nanocrystals>crystals, which is paralleled by the enhancement of the biopharmaceutical properties such as dissolution rate, supersaturation and bioavailability.

The presence of amorphous, nanocrystalline or crystal phase can be detected by means of Differential Scanning Calorimetry (DSC). Compared to the sharp melting peak of the drug crystal, the nanocrystals present a broader peak with a markedly lower maximum of temperature. Moreover, a decrease of the temperature maximum related to the nanocrystal melting peak is observed when the nanocrystals size decreases (I. Colombo et al. $4^{th}$ *Int. Conf. Pharm. Technol.*, 1986; F. Carli et al. *Acta Pharm. Jugosl.* 38, 361, 1988). The amorphous phase does not show any thermal event. The fraction of nanocrystals or crystals is determined by the melting enthalpy relative to melting peak relative to each form.

A technique to enhance the solubility of poorly soluble or insoluble drugs of reduced particle size consists in incorporating them into water-swellable but insoluble polymer by means of polymer swelling with a solution of the drug in a solvent; the solvent is thus removed and the drug precipitates in small particles within the polymer network; an example of such processes is described in DE 2 634 004 and DE 3 320 583, resulting in a uniform dispersion of the drug, mainly in the crystalline or nanocrystalline form.

An number of studies have been performed on the activation of drugs by high-energy co-grinding processes, i.e. by grinding together, in the same grinding chamber, both the drug and the supporting polymer; grinding is performed under high-energy conditions. For instance, U.S. Pat. No. 4,639,670 describes the conversion of crystalline drugs into a more activated form, obtained by co-grinding a crystalline drug with a swellable polymer such as cross-linked polyvinylpyrrolidone: this process is performed in dry conditions. In a modification of this process, U.S. Pat. No. 5,449,521 teaches that when co-grinding of drug and polymer is performed in a solvent-enriched environment, e.g. in presence of solvent vapours able to dissolve the active principle, a higher activation of the active principle is obtained. In U.S. Pat. No. 5,225,192 (M. L. Lovrecich) a process is claimed in which a polymer is first loaded with a drug by co-grinding in dry conditions; the product is then treated with a non-aqueous organic solvent in gaseous or liquid form: this process obtains a composite where the drug is mainly concentrated on the outer surface of the particles of polymeric carrier; with respect to its starting composition, the thus treated drug is present with an increased nanocrystal fraction and a reduced amorphous fraction: as a result the drug is more stabilised, but its activation level is lowered.

Although some improvement have been reported in the ability to activate poorly soluble drugs, a constant need is still present for pharmaceutical compositions with improved dissolution times and improved bioavailability. In particular, the need is highly felt for compositions with a higher the level of drug amorphisation, thus with increased solubility and bioavailability.

SUMMARY OF THE INVENTION

The present inventors have obtained composites of water-insoluble drugs with a very high level of activation, by a process comprising co-grinding a mixture of said drug with a cross-linked polymeric carrier, followed by contacting the resulting co-ground material with water or aqueous vapours. With respect to the drug in its original state, this process causes the substantial disappearance of the insoluble crystalline fraction, increases the amorphous fraction, and reduces both the nanocrystal fraction and the nanocrystals size. The composites obtainable by this process show increased dissolution properties and a high bioavailability. The composites further show an excellent flowability, which allows them to be processed easily into pharmaceutical formulations.

DETAILED DESCRIPTION OF THE INVENTION

Object of the present invention is a process to prepare a highly activated composite of one or more water-insoluble drugs, said process comprising the steps of: (a) subjecting said water-insoluble drug and a cross-linked polymer to co-grinding; (b) exposing the ground product of step a. to contact with water or water vapours. The resulting composite contains large amounts of drug in the easily soluble amorphous form, reduced amounts of drug in the nanocrystalline form, and is substantially free from practically insoluble drug crystals.

Water-insoluble drug useful for the present invention are those drugs belonging to the "class II" or "class IV" molecules, as defined in *FDA/CDER Guidance for Industry. Waiver of in-vivo bioavailability and bioequivalence studies for immediate-release solid oral dosage forms based on a Biopharmaceutical Classification System. August* 2000. Examples of water-insoluble drugs belonging to this class are cox-2 inhibitors, antiinflammatory drugs such as nimesulide, piroxicam, naproxene, ketoprofen, ibuprofen and diacerheine, antifungal drugs such as griseofulvin, itraconazole, fluconazole, miconazole and ketonazole, bronchodilators/anti-asthmatic drugs such as zafrilukast, salbutamol, beclomethasone, flunisolide, clenbuterol, salmeterol and budesonide, steroids such as estradiol, estriol, progesterone, megestrol acetate, medroxyprogesterone acetate, antihypertensive/antithrombotic/vasodilator drugs such as nefedipine, nicergoline, nicardipine, lisinopril, enalapril, nicorandil, celiprolol and verapamil, benzodiazepines such as temazepam, diazepam, lorazepam, fluidiazepam, medazepam and oxazolam, anti-migraine drugs such as zolmitriptan and sumatriptan, antilipoproteinemic drugs such as fenofibrate, lovastatin, atorvastatin, fluvastatin, and simvastatin, anti-viral/antibacterial drugs such as tosufloxacin, ciprofloxacin, ritonavir, saquinavir, nelfinavir, acyclovir and indinavir, immunodepressant drugs such as tacrolimus, rapamycine and didanisine, anti-histaminic drugs such as loratadine, antitumour drugs such as etoposide, bicalutamide, tamoxifen, doclitaxel and paclitaxel, anti-psychotic drugs such as risperidone, antiosteoporotic drugs such as raloxifene, anti-convulsant drugs such as carbamazepin and phenytoin, analgetic/narcotic drugs such as oxycodone, hydrocodone, morphine and butorpanol, muscle relaxant such as tinazadine, anti-ulcerative drugs such as famotidine.

Typical of these drugs is their substantial insolubility in water: when administered orally, they present marked problems in dissolution, thus failing to exert any appreciable systemic pharmacological action.

The activation profile obtained by the present process is limited to and peculiar of water insoluble drugs. Nevertheless, drugs having higher solubility in water may optionally be used, in admixture with the water insoluble drug(s), in the process of the invention.

The cross-linked polymer used in the process of the present invention is chosen among those cross-linked polymers commonly used as pharmaceutical carrier; these polymers are water swellable but water-insoluble: examples are cross-linked polyvinylpyrrolidone, cross-linked sodium carboxymethylcellulose, starch (as known, starch is a naturally cross-linked product), sodium starch glycolate, pregelatinized starch, polacrilin potassium; preferred polymer is cross-linked polyvinylpyrrolidone;

According to the process of the invention (step a.), the drug and the cross-linked PVP (optionally pre-mixed) are loaded into a suitable grinding apparatus and are subjected to co-grinding; preferably the two powders are added separately into the mill. The cross-linked PVP and the water-insoluble drug are used in a ratio preferably comprised between 12:1 and 0.5:1, more preferably between 5:1 and 1:1.

The grinding apparatus is chosen among those conventionally available, e.g. a ball mill, an air jet mill, rotary mill, vibration mill, roller mill, mortar mill, planetary mill, etc. However, the co-grinding is most preferably performed under high-energy conditions, e.g. using a high-energy mill, for example a Sweco DM 3 mill. The co-grinding is suitably performed at normal conditions (i.e. at room temperature and atmospheric pressure). Said co-grinding is performed in dry conditions: by "dry conditions" it is meant that there is no addition of any solvents or solvents vapours into the grinding chamber before and during the grinding process, nor the process is performed in a solvent-enriched environment; grinding at normal conditions of ambient humidity (usually lower than 75% relative humidity) is considered as a dry condition for the purpose of the present invention.

Preferably, the co-grinding (step a.) is continued until particles having an average grain size comprised between 0.1 and 500 microns are obtained. As an example, if cross-linked PVP is used, grinding times comprised between 1 and 6 hrs, e.g. 3 hrs. are in general sufficient.

Once the grinding step is concluded, the ground material is contacted with water or aqueous vapour (step b.). This step can be performed in the same grinding chamber (though in absence of grinding action), or in any other suitable reactor; the chamber or reactor can be equipped with systems to supply the water/water vapour, such as openings or nozzles connected to a water supply; if necessary, a compressing device is present to favour the solvent input; when water vapours are supplied, an apart water heater or supply of heated water/water vapours (temperature >40° C.) is preferably connected to said opening/nozzles; in alternative, the water is heated directly when fed by suitable heating means, e.g. when passing through the opening/nozzle. Alternatively, the ground powder may be transferred into a chamber already saturated with water vapours or containing the required amount of water. During the step b., the powder is preferably maintained in an agitated status, e.g. by stirring, vibration, rotation or suspension in a fluidised bed. The step b can be performed in a single process step or in two or more independent wetting steps, using identical or different wetting techniques.

The water/aqueous vapour is added to the ground powder at least until a wetted mass is obtained; preferably however, larger amounts of water are added, since the activation and the flowability increase according to the amount of added water; as an example, a powder:water weight ratio comprised between 1:0.05 and 1:5, preferably between 1:0.1 and 1:3 can be used; higher amounts of water are also contemplated by the present invention.

The time of contact between the drug and the water/aqueous vapours can be broadly varied; preferably the contact is continued until a homogeneously wetted mass is obtained; a contact time of 5-120 min, preferably 10-40 min is normally sufficient to achieve these conditions.

As mentioned above, the above process causes a substantial increase of the amorphous fraction of water-insoluble drugs and strongly reduces or eliminates any residual original crystalline form (; it also reduces the nanocrystal fraction and the nanocrystals size. Altogether, these features ensure complete and quick dissolution in-vivo, and thus an enhanced bioavailability of the active principle. The resulting activated composites show a high dissolution rate of the water-insoluble agent, a rapid distribution of the drug throughout the various body compartments, a quick access to the target receptors, a quick onset of action and an intense effect.

The increased amorphisation of the product of the present process can be experimentally proved by the reduction of the heat of fusion relative to the nanocrystals, and by the disappearance of the melting peak relative to the original crystal (DSC analysis). The reduction of nanocrystals size is indicated by the decrease of their melting temperature.

By "amorphous drug" it is meant a state of molecular dispersion into the polymer crosslinks (no melting peak is detected by Differential Scanning Calorimetry (DSC)).

By "nanocrystals" it is meant drug particles having an average particle size which allows a lowering of the maximum of the drug melting peak of at least 0.5° C., measured by DSC, according to the following works: J. R. Blachere et al *J. Am. Cer. Soc.* 55, 306, 1972; M. Brun et al. *J. Chim. Phys.* 70, 973, 1973; M. Brun et al. *J. Chim. Phys.* 70, 979, 1973.

The product resulting from the step b. (preferably dried in order to eliminate the absorbed water) can easily be processed further into pharmaceutical formulations by techniques known in the art. The optional drying step can be performed by techniques known in the art, e.g. by drying under vacuum, heating under vacuum, freeze-drying, etc.

The product of step b. shows, once dried, a very high flowability, i.e. a flowability index of ≤26 mm, preferably of ≤20 mm, as measured with a Flotest tester (Tecnogalenica, I-Cernusco sul Naviglio): this allows an easier processing into the final pharmaceutical form. (e.g. by allowing a more precise dosage, a higher recovery of product from the reactor walls, a quicker production cycle, etc.).

The processing into final pharmaceutical form may include adding, to the product of step b., conventional additives for pharmaceutical use, such as diluents, disintegrants, effervescent agents, suspending agents, lubricants, flavours, antioxidants, etc. Examples of such final pharmaceutical forms are tablets, minitablets, capsules, microcapsules, granules, pellets, soluble or dispersible powders, sachet dosage forms, suspensions, solutions, creams, ointments, implantable articles, programmed release devices, etc; where appropriate, said formulations may be provided with a polymeric coating, allowing to mask the taste of the drug and/or to maintain integrity of the drug after administration until the target site for delivery is reached within the organism.

The present invention is now described with reference to the following non limiting examples.

EXPERIMENTAL PART

Materials and Methods

Differential Scanning Calorimetry is performed at a temperature ranging from 20 to 230° C. and a scan rate of 10° C./min in a nitrogen atmosphere. Samples of 3-6 mg are used. The following experimental data are determined:

Maximum temperature of the melting peak relative to the nanocrystalline (T1) and original crystalline (T2) forms.

Melting enthalpy relative to the nanocrystalline ($\Delta H1$) and original crystalline ($\Delta H2$) forms.

Temperature ($T1_{50\%}$) relative to 50% of the melting transition relative to the nanocrystalline form.

Amount of the nanocrystalline (% Crist. 1) and original crystalline (% Crist. 2) fractions, expressed as a percent of drug on total dry product. These fractions are determined from a calibration curve taking into account the water content.

The % of amorphous phase can be calculated with the formula

100−[% Crist 1+(% Crist 2(*))]

(*): if present.

The determination of flowability is based upon the ability of the powder to fall freely from a cylinder through a hole in a plate. The flowability index is given in millimeter diameter of the smallest hole through which the powder falls freely. The flowability index is determined using a Flotest tester (Tecnogalenica, I-Cernusco sul Naviglio).

EXAMPLE 1

1. A (Reference)

3.75 g of megestrol acetate (class II drug) and 11.25 g of crosslinked polyvinylpyrrolidone (PVP-CL) are poured into the grinding chamber of a Fritsch Pulverisette 5 mill together with the grinding balls. The process time is 15 minutes.

1.B 5 g of the preparation 1.A are kneaded into a mortar with 4.95 g of water and dried. The powder/water ratio is 1:0.9 w/w.

The products of examples 1.A-B were subjected to DSC analysis. The results are shown in the following table.

TABLE 1

| Prep. | T1 (° C.) | $T1_{50\%}$ (° C.) |
|---|---|---|
| 1.A | 208.0 | 201.9 |
| 1.B | 208.0 | 200.0 |

Compared to the reference 1.A, the preparation 1B shows a marked decrease of the nanocrystals size ($T1_{50\%}$, higher activation). The melting peak of the crystalline drug (T2) is 217° C.

EXAMPLE 2

2.A (Reference)

3.75 g of griseofulvin (class II drug) and 11.25 g of crosslinked polyvinylpyrrolidone (PVP-CL) are poured into the grinding chamber of a Fritsch Pulverisette 5 mill together with the grinding balls. The process time is 15 minutes. (Reference)

2.B 5 g of the preparation 2.A are kneaded into a mortar with 4.95 g of water and dried. The powder/water ratio is 1:0.9 w/w.

The products of examples 2.A-B were subjected to DSC analysis. The results are shown in the following table.

TABLE 2

| Prep. | T1 (° C.) | Crist. 1 (%) |
|---|---|---|
| 2.A | 184.5 | 64.2 |
| 2.B | 182.6 | 60.9 |

Compared to the reference, the preparation 2.B shows a marked decrease of the nanocrystalline fraction and a reduction of the nanocrystals size (higher activation). The melting peak of the crystalline drug (T2) is 218° C.

EXAMPLE 3

Reference Example: No Class II Drug

3.A 2.5 g of theophylline (no class II drug) and 12.5 g of crosslinked polyvinylpyrrolidone (PVP-CL) are poured into the grinding chamber of a Fritsch Pulverisette 5 mill together with the grinding balls. The process time is 15 minutes.

3.B 5 g of the preparation 3.A are kneaded into a mortar with 4.95 g of water and dried. The powder/water ratio is 1:0.9 w/w.

3.C 5 g of the preparation 3.A are poured into a chamber saturated with methylene chloride vapours (organic solvent) for 24 hours, and dried.

3.D 5 g of the preparation 3.A are poured into a chamber saturated with acetone vapours (organic solvent) for 24 hours and dried.

The products of examples 3.A-D were subjected to DSC analysis. The results are shown in the following table.

TABLE 3

| Prep. | T1 (° C.) | Crist. 1 (%) |
|---|---|---|
| 3.A | 168.3 | 61.3 |
| 3.B | 168.3 | 70.0 |
| 3.C | 168.0 | 67.7 |
| 3.D | 167.0 | 66.8 |

Compared to the reference 3.A, the preparations 3.B, 3.C and 3.D show an increase of the nanocrystallinity fraction (lower activation). The melting peak of the crystalline drug (T2) is 272° C.

EXAMPLE 4

Reference Example: Class II Drug/Post-Treatment with Organic Solvent

4.A 3.75 g of griseofulvin (class II drug) and 11.25 g of crosslinked polyvinylpyrrolidone (PVP-CL) are poured into the grinding chamber of a Fritsch Pulverisette 5 mill together with the grinding balls. The process time is 15 minutes.

4.B 5 g of the preparation 4.A are poured into a chamber saturated with methylene chloride vapours (organic solvent) for 24 hours, and dried.

The products of examples 4.A-B were subjected to DSC analysis. The results are shown in the following table.

TABLE 4

| Prep. | T1 (° C.) | Crist. 1 (%) |
|---|---|---|
| 4.A | 184.5 | 64.2 |
| 4.B | 187.7 | 71.2 |

Compared to the reference 4.A, the preparation 4.B shows an increase of the nanocrystalline fraction and of the nanocrystals size (lower activation). The melting peak of the crystalline drug (T2) is 218° C.

The examples 3C, 3D and 4B show that when the wetting treatment is performed with organic solvents, the resulting effect is a generalised increase in nanocrystal fraction and of nanocrystals size, i.e. a lowering of the activation state, indiscriminately for both class II drugs (griseofulvin) and non-class II drugs (theophylline).

The example 4B shows that when the wetting treatment of class II drugs is performed with an organic solvent in place of water, no increase in the activation is present, on the contrary the activation level is lowered.

Altogether, these data highlight the criticality and selectivity of the claimed process, with respect to the activation of water-insoluble drugs.

The invention claimed is:

1. A process to prepare a pharmaceutical form of one or more water-insoluble drugs, consisting of the following steps:
    (a) co-grinding a water-insoluble drug and a cross-linked polymer in dry conditions to provide a ground product containing the water-insoluble drug;
    (b) exposing the ground product to exclusively water or water vapours to provide a composite, wherein the water-insoluble drug present in the composite has a decreased residual crystallinity and decreased nanocrystal fraction and size, as measured by differential scanning calorimetry, compared to the water-insoluble drug prior to co-grinding;
    (c) drying the composite of (b) in order to eliminate absorbed water; and
    (d) processing the dried composite of (c) into a pharmaceutical form.

2. The process according to claim 1, wherein said co-grinding is performed under high energy conditions.

3. The process according to claim 1, wherein said cross-linked polymer is selected from the group consisting of cross-linked polyvinylpyrrolidone, cross-linked sodium carboxymethylcellulose, starch, sodium starch glycolate, pregelatinized starch, and polacrilin potassium.

4. The process according to claim 1, wherein the weight ratio of cross-linked polymer to drug is from 12:1 to 0.5:1.

5. The process according to claim 1, wherein step (a) is performed for from 1 hour to 6 hours.

6. The process according to claim 1, wherein exposing the ground product to water or water vapour is performed for from 5 minutes to 120 minutes.

7. The process according to claim 1, wherein in step (b) the ground product is maintained in an agitated status.

8. The process according to claim 1, wherein the ground product/water weight ratio is from 1:0.05 to 1:5.

9. The process according to claim 1, wherein the ground product/water weight ratio is from 1:0.1 to 1:3.

10. The process according to claim 1, wherein the weight ratio of cross-linked polymer to drug is from 5:1 to 1:1.

* * * * *